United States Patent [19]

Nishikawa et al.

[11] Patent Number: 6,008,358

[45] Date of Patent: Dec. 28, 1999

[54] PROCESS FOR THE PREPARATION OF PIPERIDINYLIDENE DERIVATIVE

[75] Inventors: Takenobu Nishikawa; Nobuo Seido, both of Kanagawa, Japan

[73] Assignee: Takasago International Corporation, Tokyo, Japan

[21] Appl. No.: 09/069,114

[22] Filed: Apr. 29, 1998

[30] Foreign Application Priority Data

Mar. 31, 1998 [JP] Japan .................................. 10-103748

[51] Int. Cl.⁶ ..................... C07D 211/34; C07D 211/60; C07D 211/76
[52] U.S. Cl. .......................... 546/238; 546/230; 546/290
[58] Field of Search ..................... 546/238, 290, 546/230

[56] References Cited

PUBLICATIONS

Bhandari K et al. Indian Journal of Chemistry. 17B, 104–106, Feb. 1979.

Granik et al. Chem. Heterocycl. Compd. 9, 880–883, 1973.

Bhandari, et al., "Chemistry of Lactim Ethers: Part II–Reactions with Amines & Carbanions[(a)]," *Indian Journal of Chemistry*, vol. 17B, Feb., 1979, pp. 104–106.

*Primary Examiner*—Evelyn Mei Huang
*Attorney, Agent, or Firm*—Sughrue, Mion, Zinn, Macpeak & Seas, PLLC

[57] ABSTRACT

Disclosed is a process for economic, safe and simple production of a 2-phenyl-2-(2'-piperidinylidene)acetate derivative at a reduced number of steps in a high yield, which comprises allowing 2,3,4,5-Tetrahydro-6-methoxypyridine and a benzyl cyanide derivative represented by the following general formula (2):

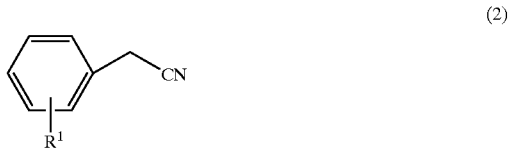

(2)

wherein $R^1$ represents a hydrogen atom, a lower alkyl group, a lower alkoxy group, a halogen atom or an amino group, to undergo condensation reaction in the presence of an organic base such as 1,8-diazabicyclo[5.4.0]-7-undecene or a transition metal complex as a catalyst to produce a 2-phenyl-2-(2'-piperidinylidene)acetonitrile derivative represented by the following general formula (4):

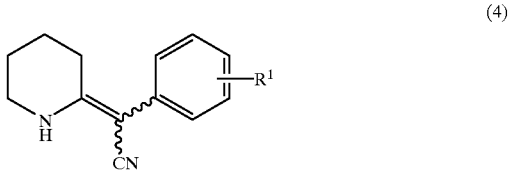

(4)

wherein $R^1$ is as defined above; and the wavy line indicates a geometrical isomer, and then reacting with an alcohol in the presence of hydrogen chloride.

5 Claims, No Drawings

PROCESS FOR THE PREPARATION OF PIPERIDINYLIDENE DERIVATIVE

FIELD OF THE INVENTION

The present invention relates to a process for the preparation of a 2-phenyl-2-(2'-piperidinylidene)acetate derivative useful as a synthesis intermediate of an optically active 2-phenyl-2-(2'-piperidinyl)acetate derivative of the following general formula (7):

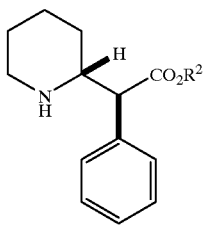

(7)

wherein $R^2$ represents a lower alkyl group having 1 to 4 carbon atoms as a key intermediate of the antidepressant described below.

BACKGROUND OF THE INVENTION

As an antidepressant there has already been commercially available methyl threo-2-phenyl-2-(2'-piperidinyl)acetate hydrochloride (trade name: Ritalin) in the form of racemic modification. It is also known that methyl threo-2-phenyl-2-(2'-piperidinyl)acetate hydrochloride exhibits a pharmacologic activity about 5 times higher in the form of a specific stereoisomer than in the form of other stereoisomers (U.S. Pat. No. 2,957,880).

Further, the structural analysis of an optically active methyl 2-phenyl-2-(2'-piperidinyl)acetate, which exhibits a higher pharmacologic activity than Ritalin as an antidepressant, has been under way. A report has been made on the absolute configuration of these optically active materials (*J. Med. Chem.*, 12, 266, 1969). A method for economic and simple preparation of such an optically active 2-phenyl-2-(2'-piperidinyl)acetate derivative from a 2-phenyl-2-(2'-piperidinylidene)acetate derivative has already been applied for patent (Japanese Patent Application No. 9-72570).

No reports have been made on method for the preparation of a 2-phenyl-2-(2'-piperidinylidene)acetate derivative from a 2-phenyl-2-(2'-piperidinylidene) acetonitrile derivative. Thus, it has been keenly desired to establish such a preparation method.

As a method for the synthesis of a 2-phenyl-2-(2'-piperidinylidene)acetonitrile derivative there is disclosed a method which comprises reacting piperidone (formula (8)) as a starting material with diphosphorus pentasulfide to synthesize a thiolactam form, reacting the thiolactam form with methyl iodide (hereinafter referred to as "MeI") in the presence of potassium hydroxide to synthesize a lactim thioether form (formula (9)), and then allowing the lactim thioether form to undergo condensation reaction with benzyl cyanide in the presence of 1,5-diazabicyclo[4.3.0]-5-nonene (hereinafter referred to as "DBN") in the same amount as the lactim thioether form thus obtained to prepare 2-phenyl-2-(2'-piperidinylidene)acetonitrile (formula (4)), as carried out in the following reaction formula (*Indian J. Chem.*, Sect. B, 17B(2), 104–106, 1979).

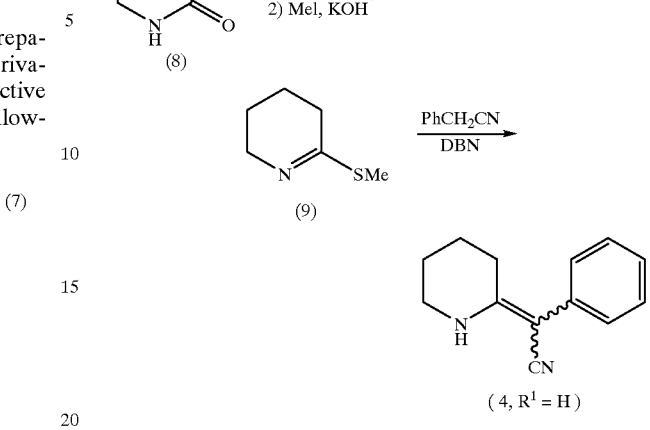

However, this synthesis method leaves something to be desired on an industrial basis. In other words, this synthesis method requires a complicated procedure and multiple reaction steps. This synthesis method is also disadvantageous in that the starting material is not easily available and DBN, which is expensive, must be used in the same amount as the intermediate. Thus, an economical preparation method feasible on an industrial basis has been desired.

Further, no reports have been made on the synthesis of a 2-phenyl-2-(2'-piperidinylidene)acetonitrile derivative involving the use of a metal complex.

SUMMARY OF THE INVENTION

The present inventors made extensive studies of the solution to the foregoing problems as to a method for the preparation of a 2-phenyl-2-(2'-piperidinylidene)acetate derivative useful as an intermediate for the synthesis of an optically active 2-phenyl-2-(2'-piperidinyl)acetate derivative. As a result, a process for economic, safe and simple production of a 2-phenyl-2-(2'-piperidinylidene)acetate derivative at a reduced number of steps in a high yield was found. Thus, the present invention has been worked out.

The present invention includes the following aspects:

1) A process for the preparation of a 2-phenyl-2-(2'-piperidinylidene)acetate derivative represented by the following general formula (6):

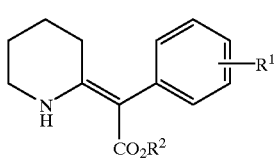

(6)

wherein $R^1$ represents a hydrogen atom, a lower alkyl group having 1 to 4 carbon atoms, a lower alkoxy group having 1 to 4 carbon atoms, a halogen atom or an amino group; and $R^2$ represents a lower alkyl group having 1 to 4 carbon atoms, which comprises allowing 2,3,4,5-tetrahydro-6-methoxypyridine represented by the following general formula (1):

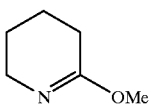

(1)

and a benzyl cyanide derivative represented by the following general formula (2):

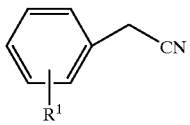

(2)

wherein $R^1$ is as defined above,
to undergo condensation reaction in the presence of an organic base or a transition metal complex represented by the following general formula (3):

$$ML_nX_m \qquad (3)$$

wherein M represents a transition metal selected from the group consisting of nickel, ruthenium, rhodium, iridium, iron, cobalt and platinum; L represents an acetylacetonato ligand; X represents a carbonyl ligand; n represents an integer of from 1 to 3; and m represents an integer of from 0 to 2,
in an amount of 1/500 to 1/2 mol per mol of 2,3,4,5-tetrahydro-6-methoxypyridine to produce a 2-phenyl-2-(2'-piperidinylidene)acetonitrile derivative represented by the following general formula (4):

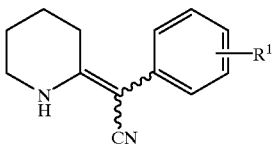

(4)

wherein $R^1$ is as defined above; and the wavy line indicates a geometrical isomer,
and then reacting the 2-phenyl-2-(2'-piperidinylidene) acetonitrile derivative thus obtained with an alcohol represented by the following general formula (5):

$$R^2OH \qquad (5)$$

wherein $R^2$ is as defined above,
in the presence of hydrogen chloride.

2) The process for the preparation of a 2-phenyl-2-(2'-piperidinylidene)acetate derivative according to Clause (1), wherein said organic base comprises one or more organic bases selected from the group consisting of triethylamine, tributylamine, ethyldiisopropylamine, dimethylaniline, pyridine, N-methylpyridine, 1,8-diazabicyclo[5.4.0]-7-undecene (DBU), 1,5-diazabicyclo[4.3.0]-5-nonene (DBN), 1,4-diazabicyclo[2.2.2]-octane (DABCO) and tetramethylguanidine (TMG).

3) The process for the preparation of a 2-phenyl-2-(2'-piperidinylidene)acetate derivative according to Clause (1), wherein said organic base is 1,8-diazabicyclo[5.4.0]-7-undecene.

4) The process for the preparation of a 2-phenyl-2-(2'-piperidinylidene)acetate derivative according to Clause (1), wherein said transition metal complex comprises one or more transition metal complexes selected from the group consisting of $Ni(acac)_2 4H_2O$, $Ni(acac)_2$, $Rh(acac)_3$, $Ru(acac)_2$, $Ir(acac)_3$, $Fe(acac)_3$, $Co(acac)_3$ and $[Pt(acac)_2]$ wherein acac represents an acetylacetonato ligand.

5) The process for the preparation of a 2-phenyl-2-(2'-piperidinylidene)acetate derivative according to Clause (1), wherein said transition metal complex is $Ni(acac)_2 4H_2O$ wherein acac represents an acetylacetonato ligand.

DETAILED DESCRIPTION OF THE INVENTION

The present invention will be further described hereinafter.

In the present invention, the lower alkyl group having 1 to 4 carbon atoms represented by $R^1$ is a methyl group, an ethyl group, a propyl group, an isopropyl group, a butyl group or a tert-butyl group. The lower alkoxy group having 1 to 4 carbon atoms represented by $R^1$ is a methoxy group, an ethoxy group, a propoxy group, an isopropoxy group or a butoxy group. The halogen group represented by $R^1$ is a fluorine atom, a chlorine atom, a bromine atom or an iodine atom.

Examples of the benzyl cyanide derivative represented by the general formula (2) include phenylacetonitrile, 2-methylphenylacetonitrile, 3-methylphenylacetonitrile, 4-methylphenylacetonitrile, 2-ethylphenylacetonitrile, 3-ethylphenylacetonitrile, 4-ethylphenylacetonitrile, 2-propylphenylacetonitrile, 3-propylphenylacetonitrile, 4-propylphenylacetonitrile, 2-methoxyphenylacetonitrile, 3-methoxyphenylacetonitrile, 4-methoxyphenylacetonitrile, 2-ethoxyphenylacetonitrile, 3-ethoxyphenylacetonitrile, 4-ethoxyphenylacetonitrile, 2-propoxyphenylacetonitrile, 3-propoxyphenylacetonitrile, 4-propoxyphenylacetonitrile, o-chlorophenylacetonitrile, m-chlorophenylacetonitrile, p-chlorophenylacetonitrile, o-bromophenylacetonitrile, m-bromophenylacetonitrile, p-bromophenylacetonitrile, o-fluorophenylacetonitrile, m-fluorophenylacetonitrile, and p-fluorophenylacetonitrile.

2,3,4,5-Tetrahydro-6-methoxypyridine (1), which is a starting material of the present invention, can be easily obtained by any known method as described in *Helv. Chem. Acta.*, 54, 513, 1971. This method involves the addition of dimethylsulfuric acid to commercially available piperidone which is then heated. As the benzyl cyanide derivative (2) there may be used a commercially available product.

From the standpoint of rapidity of progress of reaction, the amount of the organic base to be used is preferably from 1/500 to 1/2 mol, particularly from 1/100 to 1/3 mol per mol of the starting material (Compound 1).

The transition metal complex is represented by the general formula (3):

$$ML_nX_m \qquad (3)$$

wherein M represents a transition metal such as nickel, ruthenium, rhodium, iridium, iron, cobalt and platinum; L represents an acetylacetonato ligand (hereinafter referred to as "acac"); X represents a carbonyl ligand; n represents an integer of from 1 to 3; and m represents an integer of from 0 to 2. Preferred examples of the transition metal complex to be used herein from the standpoint of yield include $Ni(acac)_2 4H_2O$, $Ni(acac)_2$, $Rh(acac)_3$, $Ru(acac)_2$, $Ir(acac)_3$, $Fe(acac)_3$, $Co(acac)_3$ and $[Pt(acac)_2]$. Particularly preferred among these transition metal complexes is $Ni(acac)_2 4H_2O$.

The amount of the transition metal complex to be used is preferably from 1/500 to 1/2 mol, particularly from 1/100 to 1/3 mol per mol of the starting material.

The temperature at which the present reaction occurs is from 100° C. to 200° C., preferably from 120° C. to 170° C.

Subsequently, 2-phenyl-2-(2'-piperidinylidene) acetonitrile (4) can be purified through silica gel chromatography, and then reacted with an alcohol in the presence of hydrochloric acid to obtain a 2-phenyl-2-(2'-piperidinylidene) acetic acid derivative (6).

As the alcohol there may be used methanol, ethanol or isopropanol, preferably methanol.

The temperature at which the present reaction occurs is from 30° C. to 100° C., preferably from 40° C. to 70° C.

The 2-phenyl-2-(2'-piperidinylidene)acetic acid derivative (6) thus obtained can then be allowed to undergo hydrogenation reaction in accordance with the method described in Japanese Patent Application No. 9-72570 to obtain an optically active 2-phenyl-2-(2'-piperidyl)acetate derivative.

In accordance with the present invention, a 2-phenyl-2-(2'-piperidinylidene)acetic acid derivative (6) which is very important as a key intermediate of antidepressant can be obtained safely at low cost by a method involving a less number of steps than ever.

EXAMPLES

The present invention will be further described in the following examples, but the present invention should not be construed as being limited thereto.

The physical properties as used hereinafter were determined by means of the following measuring equipments under the following conditions.

1) Nuclear magnetic resonance:
   $^1$H-NMR; AM400 (400 MHz) (produced by Bruker, Inc.)
   $^{13}$C-NMR; AM400 (100 MHz) (produced by Bruker, Inc.)
   Internal standard substance: Tetramethylsilane
2) High-performance liquid chromatography (HPLC):
   LC-7000 Series (produced by Hitachi., Ltd.)
   Column: ODS-2 (produced by GL Sciences Inc.)
   Effluent: 7:3 by volume mixture of acetonitrile and water
   Detector: Ultraviolet absorption spectrophotometer (254 nm)
   Flow rate: 0.4 ml/min.
3) Mass spectrometry (MASS):
   M-80B (produced by Hitachi., Ltd.)
4) Melting point:
   MP-500D (produced by Yanaco)
5) Gas chromatography:
   5890 Series II (produced by Hewlett-Packard, Ltd.)
   Column: Neutrabond-1 (produced by GL Sciences Inc.)
   Inlet temperature: 220° C.
   Detector temperature: 250° C.
   Temperature: 4° C./min. between 50° C. and 200° C.

Example 1

(1) Synthesis of 2-phenyl-2-(2'-piperidinylidene) acetonitrile (4a)

Into a 30 ml eggplant type flask were charged 5.0 g (44.2 mmol) of 2,3,4,5-tetrahydro-6-methoxypyridine, 10.20 ml (88.4 mmol) of benzyl cyanide and 673 mg (4.42 mmol) of DBU. The mixture was then heated to a temperature of 150° C. in a nitrogen stream for 18 hours. The disappearance of the starting materials was confirmed by gas chromatography. The reaction mixture was then allowed to cool to room temperature.

Subsequently, the reaction mixture was concentrated under reduced pressure by an evaporator. The resulting residue was purified through silica gel column chromatography (6:1 by volume mixture of hexane and ethyl acetate) to obtain 6.2 g (yield: 71%) of 2-phenyl-2-(2'-piperidinylidene)acetonitrile (4a) in the form of white crystal.

The product thus obtained exhibited the following physical properties:

m.p.: 112–114° C.

$^1$H-NMR (CDCl$_3$/Me$_4$Si) δ: 1.78 (m, 4H), 2.79 (m, 2H), 3.17 (m, 2H), 5.48 (br, 1H), 7.18–7.40 (m, 5H)

$^{13}$C-NMR (CDCl$_3$/Me$_4$Si) δ: 20.23, 22.70, 28.00, 42.40, 122.56, 126.80, 128.84, 129.35, 133.63, 157.35

MS: 198 (M$^+$), 169, 155, 141, 115, 105, 82, 55, 43

(2) Synthesis of methyl 2-phenyl-2-(2'-piperidinylidene) acetate (6a)

5.0 g (25.2 mmol) of 2-phenyl-2-(2'-piperidinylidene) acetonitrile (4a) obtained in the foregoing step (1) was measured out in a 100 ml eggplant type flask. To the material was then added 50 ml of methanol. The flask was then cooled over an ice bath. Hydrogen chloride gas was then blown through the reaction mixture for 1 hour. After 1 hour, the reaction mixture was heated to a temperature of 45° C. where it was then stirred for 18 hours. Thereafter, the reaction mixture was allowed to cool to room temperature. Excess methanol was then distilled off under reduced pressure by an evaporator. To the residue was then added 50 ml of ethyl acetate. To the solution was then added a 2N sodium hydroxide solution until it became alkaline. The mixture was then subjected to extraction by a separatory funnel. The resulting organic phase was then washed with saturated sodium chloride solution. The organic phase was then dried over 1 g of magnesium sulfate anhydride. The mixture was then filtered. The resulting filtrate was then concentrated under reduced pressure to obtain 5.82 g of a concentrate. To the concentrate thus obtained was then added 25 ml of methanol. The mixture was then heated to a temperature of 50° C. until a uniform solution was obtained. Subsequently, the solution was allowed to cool to room temperature where it was then stirred for 18 hours to cause recrystallization. As a result, 4.08 g (yield: 70.1%) of methyl 2-phenyl-2-(2'-piperidinylidene)acetate was obtained in the form of colorless crystal.

The product thus obtained exhibited the following physical properties:

m.p.: 115–117° C.

$^1$H-NMR (CDCl$_3$/Me$_4$Si) δ: 1.56 (m, 2H), 1.73 (m, 2H), 2.11 (t, J=6.5 Hz, 2H), 3.38 (m, 2H), 3.55 (s, 3H), 7.13 (m, 2H), 7.23 (m, 3H), 9.71 (br, 1H)

$^{13}$C-NMR (CDCl$_3$) δ: 19.96, 22.32, 27.78, 41.41, 50.48, 94.59, 126.01, 127.91, 132.38, 138.24, 161.40, 170.39

MS: 231 (M$^+$), 198, 170, 143, 115, 84, 55

Examples 2 to 4

(1) Synthesis of 2-phenyl-2-(2'-piperidinylidene) acetonitrile (4a)

The procedure of the step (1) of Example 1 was followed except that as the organic base there was used DBN, TMG and DABCO, respectively, instead of DBU. The results are set forth in Table 1.

TABLE 1

| Example No. | Organic base | % Yield |
| --- | --- | --- |
| 2 | DBN | 61.5 |
| 3 | TMG | 48.0 |
| 4 | DABCO | 58.5 |

Examples 5 to 7

(1) Synthesis of 2-phenyl-2-(2'-piperidinylidene) acetonitrile (4a)

The procedure of the step (1) of Example 1 was followed except that the amount of DBU to be used as an organic base was changed from 4.42 mmol to 0.44 mmol, 2.21 mmol and 11.05 mmol, respectively. The results are set forth in Table 2.

TABLE 2

| Example No. | Amount of organic base (mmol) | % Yield |
| --- | --- | --- |
| 5 | 0.44 | 49.0 |
| 6 | 2.21 | 66.0 |
| 7 | 11.05 | 73.0 |

Comparative Examples 1 to 3

(1) Synthesis of 2-phenyl-2-(2'-piperidinylidene) acetonitrile (4a)

The procedure of the step (1) of Example 1 was followed except that the amount of DBU to be used as an organic base was changed from 4.42 mmol to 0 mmol, 0.044 mmol and 0.022 mmol, respectively. The results are set forth in Table 3.

TABLE 3

| Comparative Example No. | Amount of organic base (mmol) | % Yield |
| --- | --- | --- |
| 1 | 0 | 5.0 |
| 2 | 0.044 | 12.0 |
| 3 | 0.022 | 13.0 |

Example 8

(1) Synthesis of 2-phenyl-2-(2'-piperidinylidene) acetonitrile (4a)

Into a 30 ml eggplant type flask were charged 0.5 g (4.42 mmol) of 2,3,4,5-tetrahydro-6-methoxypyridine, 0.51 ml (4.42 mmol) of benzyl cyanide and 25 mg (0.1 mmol) of Ni(acac)$_2$4H$_2$O. The reaction mixture was then heated to a temperature of 150° C. in a nitrogen stream for 40 hours. The reaction mixture was then allowed to cool to room temperature.

Subsequently, the reaction solution was concentrated under reduced pressure by an evaporator. The resulting residue was then purified through silica gel column chromatography (6:1 by volume mixture of hexane and ethyl acetate) to obtain 486 mg (yield: 55.6%) of 2-phenyl-2-(2'-piperidinylidene)acetonitrile in the form of white crystal.

Examples 9 to 11

(1) Synthesis of 2-phenyl-2-(2'-piperidinylidene) acetonitrile (4a)

The procedure of the step (1) of Example 1 was followed except that as the transition metal complex there was used Rh(acac)$_3$, Rh(CO)$_2$(acac) and Ru(acac)$_2$, respectively, instead of Ni(acac)$_2$4H$_2$O. The results are set forth in Table 4.

TABLE 4

| Example No. | Transition metal complex | % Yield |
| --- | --- | --- |
| 9 | Rh(acac)$_3$ | 32.0 |
| 10 | Rh(CO)$_2$(acac) | 39.4 |
| 11 | RU(acac)$_2$ | 46.4 |

Example 12

(1) Synthesis of 2-(p-chlorophenyl)-2-(2'-piperidinylidene) acetonitrile (4b)

Into a 30 ml eggplant type flask were charged 1 g (8.84 mmol) of 2,3,4,5-tetrahydro-6-methoxypyridine, 1.34 g (8.84 mmol) of p-chlorophenylacetonitrile and 132 µl (0.84 mmol) of DBU. The reaction mixture was then heated to a temperature of 150° C. in a nitrogen stream for 18 hours. The reaction mixture was then allowed to cool to room temperature. Subsequently, the reaction solution was concentrated under reduced pressure by an evaporator. The resulting residue was then purified through silica gel column chromatography (6:1 by volume mixture of hexane and ethyl acetate) to obtain 1.699 g (yield: 82.9%) of 2-p-chlorophenyl-2'-(2-piperidinylidene)acetonitrile in the form of white crystal.

The product thus obtained exhibited the following physical properties:

m.p.: 120–122° C.

$^1$H-NMR (CDCl$_3$/Me$_4$Si) δ: 1.64 (m, 0.5H), 1.80 (m, 3.5H), 2.47 (t, J=6.5 Hz, 0.45H), 2.78 (m, 1.55H), 3.17 (m, 2H), 3.19 (m, 1.55H), 3.34 (m, 0.45H), 5.40 (br, 0.77H), 5.53 (br, 0.23H), 7.13–7.36 (m, 4H)

$^{13}$C-NMR (CDCl$_3$/Me$_4$Si) δ: 20.08, 20.25, 22.64, 22.68, 26.56, 28.00, 37.90, 42.42, 42.67, 122.14, 128.54, 129.53, 130.17, 130.53, 131.67, 132.12, 132.44, 132.68, 157.74, 159.92

MS: 232 (M$^+$), 196, 169, 155, 140, 123, 114, 92, 82, 55, 43

(2) Synthesis of methyl 2-(p-chlorophenyl)-2-(2'-piperidinylidene)acetate (4b)

1.0 g (4.30 mmol) of the product (3b) was measured out in a 50 ml eggplant type flask. To the material was then added 10 ml of methanol. The flask was then cooled over an ice bath. Hydrogen chloride gas was then blown through the reaction mixture for 1 hour. After 1 hour, the reaction mixture was heated to a temperature of 45° C. where it was then stirred for 4 hours. The reaction mixture was allowed to cool to room temperature. Excess methanol was then distilled off under reduced pressure by an evaporator. Subsequently, to the residue was then added 20 ml of ethyl acetate. To the solution was then added a 2N sodium hydroxide solution until it became alkaline. The mixture was then subjected to extraction by a separatory funnel. The resulting organic phase was then washed with saturated sodium chloride solution. The organic phase was then dried over 1 g of magnesium sulfate anhydride. The mixture was then filtered. The resulting filtrate was then concentrated under reduced pressure. The resulting residue was then purified through silica gel column chromatography (4:3 by volume mixture of hexane and ethyl acetate) to obtain 801 mg (yield: 70.1%) of methyl 2-(p-chlorophenyl)-2-(2'-piperidinylidene)acetate in the form of white crystal.

The product thus obtained exhibited the following physical properties:

9 m.p.: 111–113° C.

$^1$H-NMR (CDCl$_3$/Me$_4$Si) δ ppm: 1.58 (m, 2H), 1.75 (m, 2H), 2.09 (t, J=6.5 Hz, 2H), 3.37 (m, 2H), 3.55 (s, 3H), 7.03–7.27 (m, 4H), 9.73 (br, 1H)

$^{13}$C-NMR (CDCl$_3$) δ ppm: 20.54, 22.90, 28.44, 42.07, 51.16, 93.94, 128.79, 132.53, 134.39, 137.41, 162.10, 170.72

MS: 265 (M$^+$), 232, 204, 170, 149, 139, 125, 115, 97, 82, 55, 42

Example 13

(1) Synthesis of 2-(p-methoxyphenyl)-2-(2'-piperidinylidene) acetonitrile (4c)

Into a 30 ml eggplant type flask were charged 1 g (8.84 mmol) of 2,3,4,5-tetrahydro-6-methoxypyridine, 1.30 ml (8.84 mmol) of p-methoxyphenylacetonitrile and 132 μl (0.84 mmol) of DBU. The reaction mixture was then heated to a temperature of 150° C. in a nitrogen stream for 40 hours. The reaction mixture was then allowed to cool to room temperature. Subsequently, the reaction solution was concentrated under reduced pressure by an evaporator. The resulting residue was then purified through silica gel column chromatography (6:1 by volume mixture of hexane and ethyl acetate) to obtain 1.14 g (yield: 56.7%) of 2-(p-methoxyphenyl)-2-(2'-piperidinylidene)acetonitrile in the form of white crystal.

$^1$H-NMR (CDCl$_3$/Me$_4$Si) δ ppm: 1.77 (m, 4H), 2.41 (t, J=6.4 Hz, 0.33H), 2.76 (m, 1.66H), 3.15 (m, 1.66H), 3.32 (m, 0.33H), 3.78, 3.79, (s, 3H), 5.26 (br, 0.88H), 5.38 (br, 0.12H), 6.82–7.24 (m, 4H)

$^{13}$C-NMR (CDCl$_3$/Me$_4$Si) δ ppm: 20.96, 23.49, 27.07, 28.48, 43.37, 56.04, 114.50, 115.41, 123.35, 126.68, 131.01, 131.40, 157.74, 158.65, 159.12, 159.91

MS: 288 (M$^+$), 213, 189, 171, 135, 107, 92, 77, 55, 43

(2) Synthesis of methyl 2-(p-methoxyphenyl)-2-(2'-piperidinylidene)acetate (6c)

650 mg (2.85 mmol) of the product (4c) was measured out in a 50 ml eggplant type flask. To the material was then added 7 ml of methanol. The flask was then cooled over an ice bath. Hydrogen chloride gas was then blown through the reaction mixture for 1 hour. After 1 hour, the reaction mixture was heated to a temperature of 45° C. where it was then stirred for 18 hours. The reaction mixture was allowed to cool to room temperature. Excess methanol was then distilled off under reduced pressure by an evaporator. Subsequently, to the resulting residue was added 15 ml of ethyl acetate. To the mixture was then added a 2N sodium hydroxide solution until it became alkaline. The mixture was then subjected to extraction by a separatory funnel. The resulting organic phase was then washed with saturated sodium chloride solution. The organic phase was then dried over 1 g of magnesium sulfate anhydride. The mixture was then filtered. The resulting filtrate was then concentrated under reduced pressure. The resulting residue was then purified through silica gel column chromatography (4:3 by volume mixture of hexane and ethyl acetate) to obtain 450 mg (yield: 60.5%) of methyl 2-(p-methoxyphenyl)-2-(2'-piperidinylidene)acetate in the form of white crystal.

The product thus obtained exhibited the following physical properties:

m.p.: 87.5–88.5° C.

$^1$H-NMR (CDCl$_3$/Me$_4$Si) δ: 1.51 (m, 2H), 1.71 (m, 2H), 2.11 (t, J=6.5 Hz, 2H), 3.55 (s, 3H), 3.80 (s, 3H), 6.85 (m, 2H), 7.02 (m, 2H), 9.70 (br, 1H)

$^{13}$C-NMR (CDCl$_3$) δ: 20.02, 22.34, 27.80, 41.42, 50.50, 55.12, 93.83, 113.39, 130.43, 133.24, 157.85, 161.60, 170.61

MS: 261 (M$^+$), 228, 213, 200, 186, 173, 144, 121, 82

10

Example 14

(1) Synthesis of 2-(p-tolyl)-2-(2'-piperidinylidene) acetonitrile (4d)

Into a 30 ml eggplant type flask were charged 1 g (8.84 mmol) of 2,3,4,5-tetrahydro-6-methoxypyridine, 1.10 ml (8.84 mmol) of p-methylphenylacetonitrile and 132 μl (0.84 mmol) of DBU. The reaction mixture was then heated to a temperature of 150° C. in a nitrogen stream for 40 hours. The reaction mixture was then allowed to cool to room temperature. The reaction mixture was then concentrated under reduced pressure by an evaporator. The resulting residue was then purified through silica gel column chromatography (6:1 by volume mixture of hexane and ethyl acetate) to obtain 1.20 g (yield: 64.2%) of 2-(p-tolyl)-2-(2'-piperidinylidene)acetonitrile in the form of white crystal.

The product thus obtained exhibited the following physical properties.

$^1$H-NMR (CDCl$_3$/Me$_4$Si) δ: 1.64 (m, 0.56 H), 1.78 (m, 3.44H), 2.32, 2.34 (s, 3H), 2.47 (t, J=0.39H), 2.78 (m, 1.61H), 3.16 (m, 1.61H), 3.34 (0.39H), 5.39 (br, 1H), 7.11–7.26 (m, 4H)

$^{13}$C-NMR (CDCl$_3$/Me$_4$Si) δ: 20.98, 21.13, 21.71, 21.79, 23.51, 27.20, 28.61, 43.08, 43.41, 123.30, 129.45, 129.75, 129.98, 130.68, 131.12, 136.41, 137.30, 157.77, 160.05

MS: 212 (M$^+$), 197, 183, 169, 155, 140, 129, 91, 82, 43

(2) Synthesis of methyl 2-(p-tolyl)-2-(2'-piperidinylidene) acetate (6c)

1.0 g (4.71 mmol) of the product (4c) was measured out in a 50 ml eggplant type flask. To the material was then added 10 ml of methanol. The flask was then cooled over an ice bath. Hydrogen chloride gas was then blown through the reaction mixture for 1 hour. After 1 hour, the reaction mixture was heated to a temperature of 45° C. where it was then stirred for 23 hours. The reaction mixture was allowed to cool to room temperature. Excess methanol was then distilled off under reduced pressure by an evaporator. Subsequently, to the residue was then added 20 ml of ethyl acetate. To the solution was then added a 2N sodium hydroxide solution until it became alkaline. The mixture was then subjected to extraction by a separatory funnel. The resulting organic phase was then washed with saturated sodium chloride solution. The organic phase was then dried over 1 g of magnesium sulfate anhydride. The mixture was then filtered. The resulting filtrate was then concentrated under reduced pressure. The resulting residue was then purified through silica gel column chromatography (4:3 by volume mixture of hexane and ethyl acetate) to obtain 900 mg (yield: 78.3%) of methyl 2-(p-tolyl)-2-(2'-piperidinylidene)acetate in the form of white crystal.

The product thus obtained exhibited the following physical properties:

m.p.: 52.0–52.8° C.

$^1$H-NMR (CDCl$_3$/Me$_4$Si) δ: 1.57 (m, 2H), 1.72 (m, 2H), 2.12 (t, J=6.6 Hz, 2H), 2.34 (s, 3H), 3.36 (m, 2H), 3.55 (s, 3H), 7.00 (m, 2H), 7.10 (m, 2H), 9.70 (br, 1H)

$^{13}$C-NMR (CDCl$_3$) δ: 19.99, 21.21, 22.35, 41.42, 50.49, 94.25, 128.73, 132.17, 135.15, 135.48, 161.43, 170.53

MS: 245 (M$^+$), 212, 198, 170, 142, 115, 84, 55

While the invention has been described in detail and with reference to specific embodiments thereof, it will be apparent to one skilled in the art that various changes and modifications can be made therein without departing from the spirit and scope thereof.

What is claimed is:

1. A process for the preparation of a 2-phenyl-2-(2'-piperidinylidene)acetate derivative represented by the following formula (6):

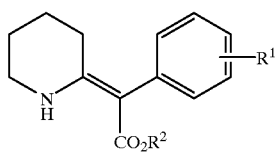

(6)

wherein R¹ represents a hydrogen atom, a lower alkyl group having 1 to 4 carbon atoms, a lower alkoxy group having 1 to 4 carbon atoms, a halogen atom or an amino group; and R² represents a lower alkyl group having 1 to 4 carbon atoms, which comprises allowing 2,3,4,5-tetrahydro-6-methoxypyridine represented by the following formula (1):

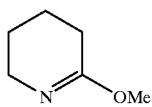

(1)

and a benzyl cyanide derivative represented by the following formula (2):

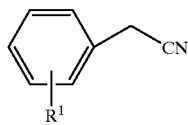

(2)

wherein R¹ is as defined above, to undergo condensation reaction in the presence of an organic base or a transition metal complex represented by the following formula (3):

$$ML_nX_m \qquad (3)$$

wherein M represents a transition metal selected from the group consisting of nickel, ruthenium, rhodium, iridium, iron, cobalt and platinum; L represents an acetylacetonato ligand; X represents a carbonyl ligand; n represents an integer of from 1 to 3; and m represents an integer of from 0 to 2, in an amount of 1/500 to ½ mol per mol of 2,3,4,5-tetrahydro-6-methoxypyridine to produce a 2-phenyl-2-(2'-piperidinylidene)acetonitrile derivative represented by the following formula (4):

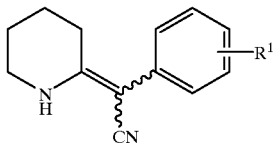

(4)

wherein R¹ is as defined above; and the wavy line indicates a geometrical isomer, and then reacting the 2-phenyl-2-(2'-piperidinylidene)acetonitrile derivative thus obtained with an alcohol represented by the following formula (5):

$$R^2OH \qquad (5)$$

wherein R² is as defined above, in the presence of hydrogen chloride.

2. The process for the preparation of a 2-phenyl-2-(2'-piperidinylidene)acetate derivative according to claim 1, wherein said organic base is one or more organic basis selected from the group consisting of triethylamine, tributylamine, ethyldiisopropylamine, dimethylaniline, pyridine, N-methylpyridine, 1,8-diazabicyclo[5.4.0]-7-undecene, 1,5-diazabicyclo[4.3.0]-5-nonene, 1,4-diazabicyclo[2.2.2]-octane and tetramethylguanidine.

3. The process for the preparation of a 2-phenyl-2-(2'-piperidinylidene)acetate derivative according to claim 1, wherein said organic base is 1,8-diazabicyclo[5.4.0]-7-undecene.

4. The process for the preparation of a 2-phenyl-2-(2'-piperidinylidene)acetate derivative according to claim 1, wherein said transition metal complex is one or more transition metal complexes selected from the group consisting of Ni(acac)₂4H₂O, Ni(acac)₂, Rh(acac)₃, Ru(acac)₂, Ir(acac)₃, Fe(acac)₃, Co(acac)₃ and [Pt(acac)₂] wherein acac represents an acetylacetonato ligand.

5. The process for the preparation of a 2-phenyl-2-(2'-piperidinylidene)acetate derivative according to claim 1, wherein said transition metal complex is Ni(acac)₂4H₂O wherein acac represents an acetylacetonato ligand.

* * * * *